US011655487B2

(12) United States Patent
Llosa

(10) Patent No.: US 11,655,487 B2
(45) Date of Patent: May 23, 2023

(54) PARTIALLY BUFFERED FREE ACID AND/OR KETONE BLEND COMPOSITIONS FOR RAPID ONSET KETOSIS AND METABOLIC THERAPY

(71) Applicant: KetoneAid, Inc., Falls Church, VA (US)

(72) Inventor: Frank Borges Llosa, Falls Church, VA (US)

(73) Assignee: KetoneAid, Inc., Falls Church, VA (US)

( * ) Notice: Subject to any disclaimer, the term of this patent is extended or adjusted under 35 U.S.C. 154(b) by 84 days.

(21) Appl. No.: 16/947,036

(22) Filed: Jul. 15, 2020

(65) Prior Publication Data
US 2020/0347413 A1 Nov. 5, 2020

Related U.S. Application Data

(63) Continuation of application No. 15/688,690, filed on Aug. 28, 2017, now abandoned.

(60) Provisional application No. 62/381,544, filed on Aug. 30, 2016.

(51) Int. Cl.
| C12P 7/26 | (2006.01) |
| A23L 33/16 | (2016.01) |
| C12P 7/52 | (2006.01) |
| A23L 33/10 | (2016.01) |
| A23L 5/00 | (2016.01) |

(52) U.S. Cl.
CPC .............. C12P 7/26 (2013.01); A23L 33/10 (2016.08); A23L 33/16 (2016.08); C12P 7/52 (2013.01); A23L 5/00 (2016.08)

(58) Field of Classification Search
None
See application file for complete search history.

(56) References Cited

U.S. PATENT DOCUMENTS

| 4,997,976 | A | 3/1991 | Brunengraber et al. |
| 5,112,865 | A | 5/1992 | Nichels et al. |
| 5,126,373 | A | 6/1992 | Brunengraber et al. |
| 6,207,856 | B1 | 3/2001 | Veech |
| 6,316,038 | B1 | 11/2001 | Veech |
| 6,323,237 | B1 | 11/2001 | Veech |
| 6,380,244 | B2 | 4/2002 | Martin et al. |
| 6,613,356 | B1 | 9/2003 | Vlahakos |
| 7,351,736 | B2 | 4/2008 | Veech |
| 8,101,653 | B2 | 1/2012 | Veech |
| 8,642,654 | B2 | 2/2014 | Clarke et al. |
| 9,034,613 | B2 | 5/2015 | Robertson et al. |
| 9,138,420 | B2 | 9/2015 | D'Agostino et al. |
| 9,211,275 | B2 | 12/2015 | Clarke et al. |
| 9,579,302 | B2 | 2/2017 | Veech et al. |
| 10,051,880 | B2 | 8/2018 | Clarke et al. |
| 10,154,982 | B2 | 12/2018 | Clarke et al. |
| 10,245,242 | B1 | 4/2019 | Millet |
| 10,292,952 | B2 | 5/2019 | Millet |
| 10,478,415 | B2 | 11/2019 | Veech et al. |
| 10,588,876 | B2 | 3/2020 | Millet |
| 10,596,129 | B2 | 3/2020 | Millet |
| 10,596,313 | B2 | 3/2020 | Gregory et al. |
| 10,736,861 | B2 | 8/2020 | Millet |
| 11,033,553 | B2 | 6/2021 | Millet |
| 11,044,932 | B1 | 6/2021 | Price et al. |
| 2003/0138384 | A1 | 7/2003 | Stephenson et al. |
| 2006/0280721 | A1 | 12/2006 | Veech et al. |
| 2010/0004194 | A1 | 1/2010 | Berg et al. |
| 2011/0237666 | A1 | 9/2011 | Clarke et al. |
| 2011/0287131 | A1 | 11/2011 | Murali et al. |
| 2012/0329742 | A1 | 12/2012 | Weg |
| 2014/0010939 | A1 | 1/2014 | Krohn et al. |
| 2014/0308719 | A1 | 10/2014 | Clarke et al. |
| 2014/0350105 | A1* | 11/2014 | D'Agostino ............. A23L 2/52 514/547 |
| 2015/0065571 | A1 | 3/2015 | Clarke et al. |
| 2015/0238494 | A1 | 8/2015 | Owoc |
| 2016/0030314 | A1 | 2/2016 | Clarke et al. |
| 2017/0266148 | A1 | 9/2017 | D'Agostino et al. |
| 2017/0296501 | A1 | 10/2017 | Lowery et al. |
| 2018/0057846 | A1 | 3/2018 | Llosa et al. |
| 2018/0195096 | A1 | 7/2018 | Veech et al. |
| 2019/0014798 | A1 | 1/2019 | Clarke et al. |
| 2019/0119705 | A1 | 4/2019 | Llosa et al. |
| 2019/0177673 | A1 | 6/2019 | Llosa et al. |
| 2019/0201366 | A1 | 7/2019 | Clarke et al. |

(Continued)

FOREIGN PATENT DOCUMENTS

| AU | 2004245567 A1 | 12/2004 |
| EP | 1755743 A2 | 2/2007 |

(Continued)

OTHER PUBLICATIONS

Burnett, A.L., "The Role of Nitric Oxide in Erectile Dysfunction: Implications for Medical Therapy," *The Journal of Clinical Hypertension* 8(s12):53-62, Wiley-Blackwell Publishing Ltd., United States (Dec. 2006).

Cox, P.J., et al., "Nutritional Ketosis Alters Fuel Preference and Thereby Endurance Performance in Athletes," *Clinical and Translational Report* 24(2):256-268, Elsevier Inc., Netherlands (Aug. 2016).

Desrochers, S., et al., "R,S-1,3-butanediol acetoacetate esters, potential alternates to lipid emulsions for total parenteral nutrition," *The Journal of Nutritional Biochemistry* 6(2):111-118, Elsevier Inc., Netherlands (Feb. 1995).

Le Sann, C., et al., "Assembly intermediates inpolyketide biosynthesis: enantioselective syntheses of beta-hydro xycarbonyl compounds," *Org Biomol Chem* 3(9):1719-1728, Royal Society of Chemistry, United Kingdom (Mar. 2005).

(Continued)

*Primary Examiner* — Christian L Fronda
(74) *Attorney, Agent, or Firm* — Sterne, Kessler, Goldstein & Fox P.L.L.C.

(57) ABSTRACT

A foodstuff can include a free acid β-hydroxybutyrate, and a base. The β-hydroxybutyrate, and base, are present at a less than 1:1 molar equivalence. Ketone Ester may also be incorporated as a component of the foodstuff.

9 Claims, 8 Drawing Sheets

(56) References Cited

U.S. PATENT DOCUMENTS

| | | |
|---|---|---|
| 2020/0121623 A1 | 4/2020 | Millet |
| 2020/0360517 A1 | 11/2020 | Clarke |
| 2020/0385331 A1 | 12/2020 | Llosa |

FOREIGN PATENT DOCUMENTS

| | | |
|---|---|---|
| WO | WO-2010021766 A1 | 2/2010 |
| WO | WO-2014153416 A1 | 9/2014 |
| WO | WO-2017156446 A1 | 9/2017 |
| WO | WO-2018115158 A1 | 6/2018 |
| WO | WO-2019104082 A1 | 5/2019 |

OTHER PUBLICATIONS

Office Action dated Mar. 22, 2019, in U.S. Appl. No. 15/688,690, Llosa, F.B., et al., filed Aug. 28, 2017, 9 pages.

Office Action dated Jul. 8, 2019, in U.S. Appl. No. 16/408,424, Llosa, F.B., filed May 9, 2019, 18 pages.

Office Action dated Jun. 16, 2020, in U.S. Appl. No. 16/167,449, Llosa, F.B., et al., filed Oct. 22, 2018, 11 pages.

Final Office Action dated Feb. 22, 2021, in U.S. Appl. No. 16/167,449, LLosa, F.B., et al., filed Oct. 22, 2018, 12 pages.

Advisory Committee on Novel Foods and Proccesses (ACNFP), "Application for the Approval of (3)-R-hydroxybutyl (3)-R-hydroxybutyrate Under Regulation (EC) No. 258/97 of the European Parliament and of the Council of Jan. 27, 1997 Concerning Novel Foods and Novel Food Ingredients," Government of the United Kingdom, United Kingdom, 69 pages (Jul. 24, 2013).

Barr, D., "The Myth of Waxy Maize Starch and the Truth Behind It All!," bodybuilding.com, accessed at URL:[https://www.bodybuilding.com/fun/waxy_maize_starch_myth.htm] on Dec. 8, 2021, 6 pages (Jan. 2019).

BENEO-Institute, "Slow release carbohydrate," isomaltulose.org, accessed at URL:[https://isomaltulose.org/home/slow-release-carb/] on Dec. 7, 2021, BENEO GmbH, Germany, 1 page.

Clarke, K., et al., "Kinetics, safety and tolerability of (R)-3-hydroxybutyl (R)-3-hydroxybutyrate in healthy adult subjects," Regulatory Toxicology and Pharmacology 63(3), 19 pages, Elsevier, Netherlands (Aug. 2012).

EndurElite, "Cluster Dextrin—The King of Carbs for Endurance Athletes," endurlite.com, accessed at URL:[https://endurelite.com/blogs/free-nutrition-supplement-and-training-articles-for-runners-and-cyclists/king-of-carbs] on Dec. 8, 2021, 6 pages (Jun. 2018).

Maresch, C. C., et al., "Low Glycemic Index Prototype Isomaltulose—Update of Clinical Trials," Nutrients 9(4):381, 12 pages, MDPI, Switzerland (Apr. 2017).

Office Action dated Apr. 15, 2021, in U.S. Appl. No. 16/736,136, Llosa, F.B., filed Jan. 7, 2020, 20 pages.

Office Action dated Sep. 10, 2021, in U.S. Appl. No. 16/168,703, Llosa, F.B., filed Oct. 23, 2018, 9 pages.

Office Action dated Apr. 28, 2022, in U.S. Appl. No. 16/168,703, Llosa, F.B., et al., filed Oct. 23, 2018, 8 pages.

Office Action dated Dec. 20, 2022, in U.S. Appl. No. 16/168,703, Llosa, F.B., et al., filed Oct. 23, 2018, 16 pages.

Office Action dated Aug. 31, 2021, in U.S. Appl. No. 16/167,449, Llosa, F.B., filed Oct. 22, 2018, 17 pages.

Office Action dated Feb. 2, 2022, in U.S. Appl. No. 17/455,826, Llosa, F.B., filed Nov. 19, 2021, 24 pages.

Office Action dated Jul. 1, 2022, in U.S. Appl. No. 17/455,826, Llosa, F.B., filed Nov. 19, 2021, 19 pages.

\* cited by examiner (D/L)-1,3-butanediol

D-β-hydroxybutyrate

D-β-hydroxybutyrate sodium

PARTIALLY BUFFERED FREE ACID AND/OR KETONE BLEND COMPOSITIONS FOR RAPID ONSET KETOSIS AND METABOLIC THERAPY

CROSS REFERENCE TO RELATED APPLICATION

This application claims priority to U.S. provisional application 62/381,544 filed Aug. 30, 2016 which is hereby incorporated by reference.

TECHNICAL FIELD

This invention generally relates to compositions and methods for producing near instant and/or therapeutic levels of nutritional ketosis, and in particular but not limited to compositions and methods related to the right hand enantiomer in particular in either in its pure enantiomer form or enantiomerically enriched form of a Ketone Blend, including any two or more of the following: (D)-β-hydroxybutyrate salts, (D)-β-hydroxybutyrate free acid, (D)-1,3-butanediol, and Ketone Ester, for mitochondrial health, treating other conditions, and physical performance.

BACKGROUND

The free acid form of racemic (D/L)-β-hydroxybutyrate (β-HB) has been used intravenously in the past, despite that only the (D) isomer is bioactive. At the same time its oral use has been limited due to its acidity and tolerability in the gut. (D/L)-β-HB(Na+) salt has also been used in the past, but its use has also been limited due to limitations on sodium intake. (D/L) 1,3-butanediol, which is converted in the liver to (D)-β-hydroxybutyrate free acid was considered as a possible high density food for astronauts but it is an alcohol that, in excess, causes inebriation. Any combination of the three such that none exceed their recognized daily metabolic limit, provides more rapid onset and the ability to ingest a far greater amount of (D)-β-hydroxybutyrate free acid, and/or (D)-β-hydroxybutyrate salts, (D)-1,3-butanediol, and Ketone Ester, for sustained ketosis for therapeutic applications.

SUMMARY

An aspect of the present invention can include a foodstuff having a partially buffered free acid of β-hydroxybutyrate which is defined as less than a 1:1 molar equivalent with respect to the buffering base.

An aspect can include a foodstuff having free acid (D)-β-hydroxybutyrate, and/or a (D)-β-hydroxybutyrate salt, (D)-1,3-butanediol and/or Ketone Ester. In some embodiments, the free acid (D)-β-hydroxybutyrate, and the (D)-β-hydroxybutyrate salt, and (D)-1,3-butanediol, and Ketone Ester can be in a molar ratio of 5:5:1:5. In other embodiments, they can be in a molar ratio of 5±2:5±2:2±2:5±3. In yet other embodiments, they can be in a molar ratio of 10±5:5±5:2±2:5±5. In some embodiments, the free acid β-hydroxybutyrate can be enterically encapsulated and/or with a buffer to prevent gastric degradation. The buffer can include sodium bicarbonate. In other embodiments, the β-hydroxybutyrate salt can be sodium (Na+), potassium (K+), calcium (Ca+), and/or a combination of two or more thereof. None of the products currently on the market do anything to prevent significant gastric degradation which can decrease bioavailability by 20%-50%.

Another aspect can include a foodstuff having sodium (D)-β-hydroxybutyrate, potassium (D)-β-hydroxybutyrate, and/or calcium (D)-β-hydroxybutyrate. In some embodiments, the ratio of sodium, potassium, and calcium (D)-β-hydroxybutyrate salts can be in a range of 1.75-3.5 parts sodium (D)-β-hydroxybutyrate, 2.0-3.5 parts potassium (D)-β-hydroxybutyrate, and 1.75-2.5 calcium (D)-β-hydroxybutyrate. The embodiments can further include free acid (D)-β-hydroxybutyrate. The embodiment can yet further include (D)-1,3-butanediol. The (D)-1,3-butanediol can be enantiomerically enriched, or enantiomerically pure. In yet other embodiments, the (D)-1,3-butanediol can be enantiomerically enriched or enantiomerically pure, the free acid (D)β-hydroxybutyrate can be enantiomerically enriched, or enantiomerically pure, and the (D)-β-hydroxybutyrate salt can be can be enantiomerically enriched, or enantiomerically pure. In an embodiment of the present invention, the composition may include a Ketone Ester, (D)-3-hydroxybutyl-(D)-3-hydroxybutyrate and or (D)-3-hydroxybutyl-3-hydroxyethyl butyrate, as significant therapeutic ketosis may be realized therefrom that can be enantiomerically enriched, or enantiomerically pure with respect to the (D) isomers.

An aspect can include a method for treating erectile dysfunction, including the step of administering or consuming a Ketone Blend. An aspect can include a method for treating hair loss, including the step of administering or consuming a Ketone Blend. An aspect can include a method for increasing visual acuity including the step of administering or consuming a Ketone Blend. An aspect can include a method for treating the symptoms such as fatigue and cognitive impairment associated with amyotrophic lateral sclerosis, including the step of administering or consuming a Ketone Blend. An aspect can include a method for treating concussions and/or traumatic brain injury, including the step of administering or consuming a Ketone Blend.

An aspect can include a method for enhancing physical performance, and muscle recovery, including the step of administering or consuming a Ketone Blend.

An aspect can include a mixture of enantiomerically enriched for the (D) isomer in all cases of β-hydroxybutyrate salts having enantiomerically enriched sodium β-hydroxybutyrate and/or at least one additional enantiomerically enriched β-hydroxybutyrate salt. In some embodiments, at least one additional enantiomerically enriched β-hydroxybutyrate salt can be potassium β-hydroxybutyrate and/or calcium β-hydroxybutyrate. Enantiomerically enriched is defined as greater than 50% and less than 100% for the (D) isomer of β-hydroxybutyrate salts and the (D) isomer of β-hydroxybutyrate free acid and the (D) isomer of 1,3-butanediol.

An aspect can include a foodstuff having limited racemic sodium β-hydroxybutyrate, racemic potassium β-hydroxybutyrate, and/or racemic calcium β-hydroxybutyrate in combination with the free acid (D)-β-hydroxybutyrate, and/or (D)-1,3-butanediol, and/or KE such that the preponderance of the composition is non-racemic or enantiomerically enriched.

Other features and associated advantages will become apparent with reference to the following detailed description of specific embodiments in connection with the accompanying drawings.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION

Figure 1:
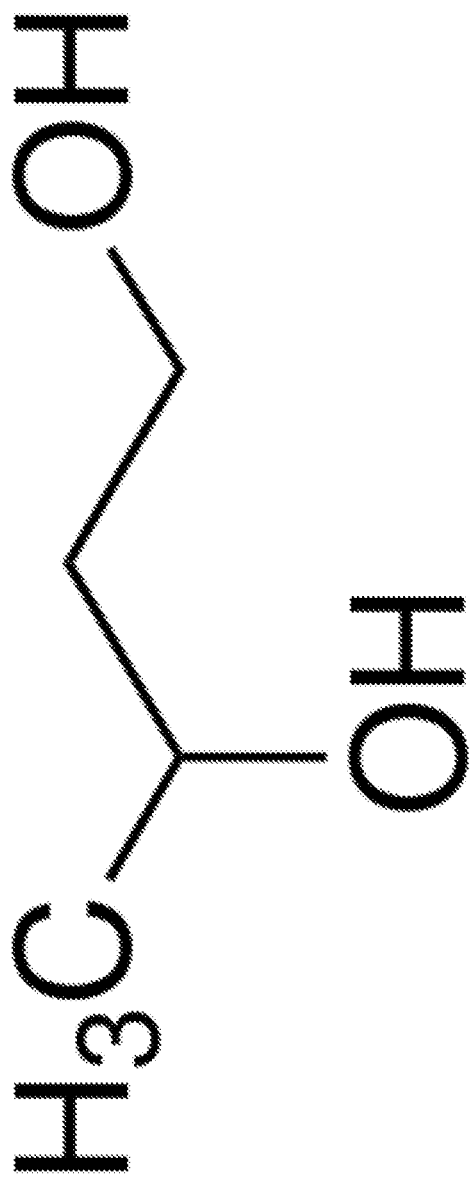
FIG. 1 is a line-angle formula of 1,3-butanediol, $C_4H_{10}O_2$.
Figure 2:
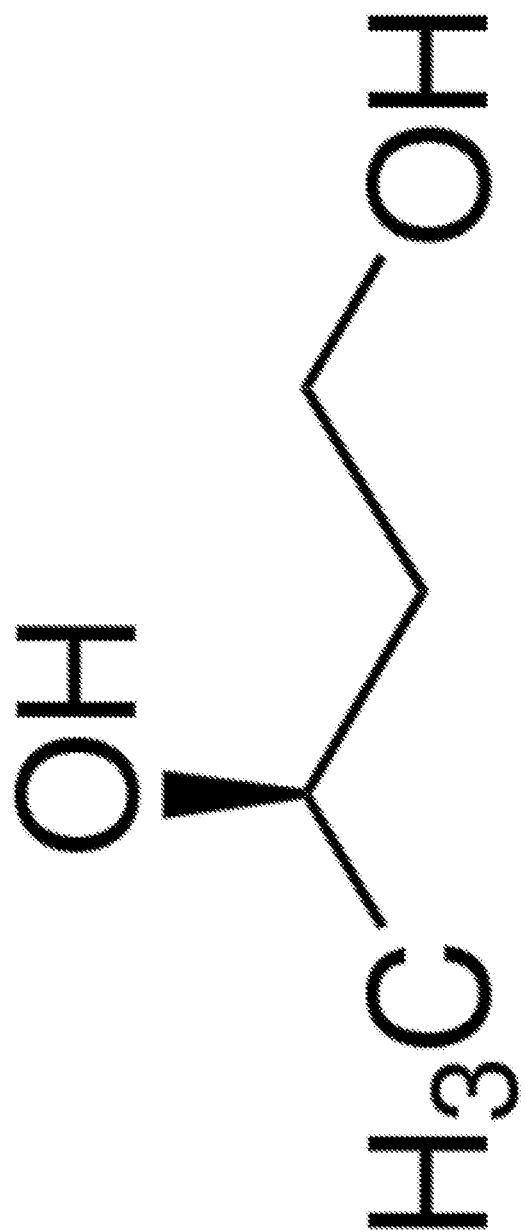
FIG. 2 is a line-angle formula of (D)-1,3-butanediol.
Figure 3:
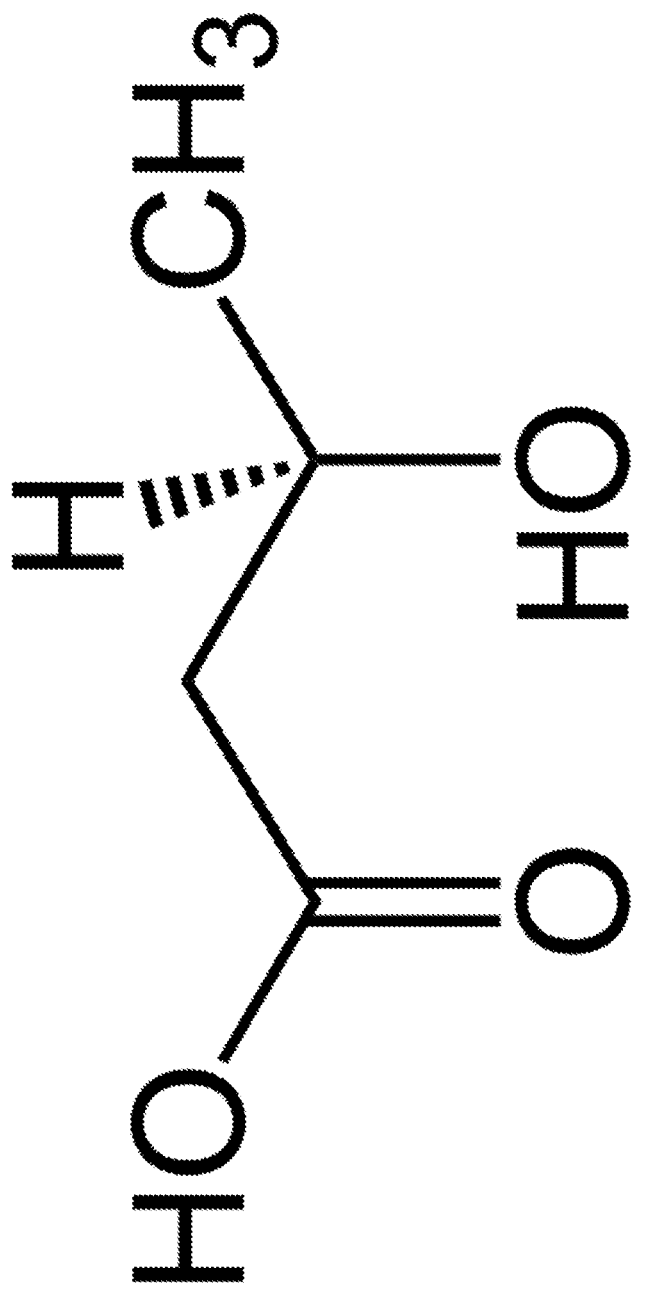
FIG. 3 is a line angle formula of (D)-β-hydroxybutyrate.
Figure 4:
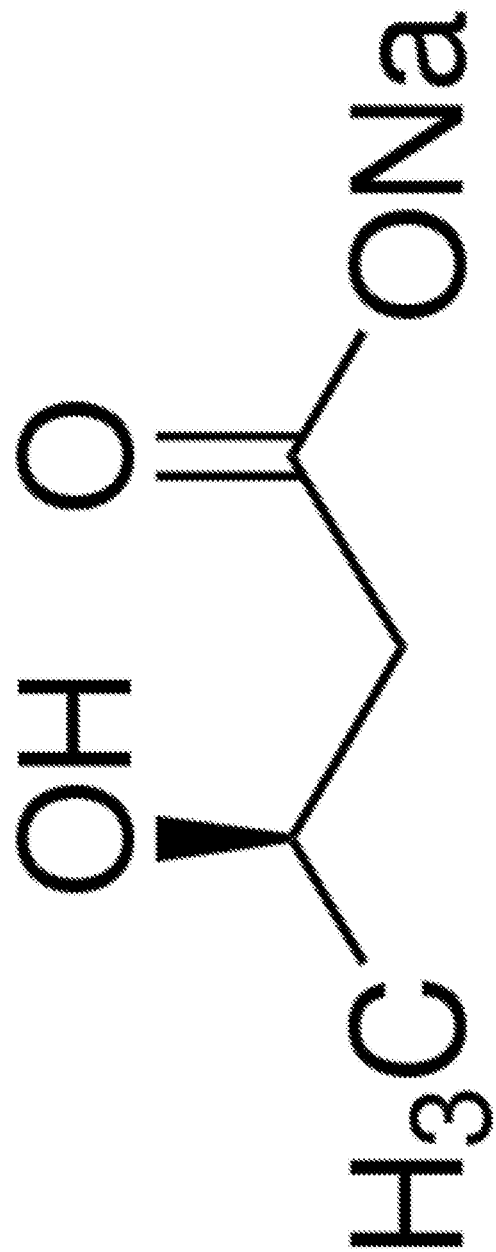
FIG. 4 is a line-angle formula of sodium (D)-β-hydroxybutyrate.

A detailed explanation of the composition of matter and process according to preferred embodiments of the present invention are described below.

Ketosis is a fat-based metabolism wherein the liver produces exclusively the (D) enantiomer of β-hydroxybutyrate. Though occurring in very small quantities as an intermediate metabolite, (L)-β-hydroxybutyrate must be distinguished from the (D) version and is only created and found in very small quantities inside the mitochondria and is never found naturally in the cytosol of any cells or circulating through the blood in any measurable amounts, a state indicated by elevated levels of ketones in the blood and in which a person's body produces ketones for fueling metabolism rather than primarily using dietary forms of glucose or metabolizing glycogen to make glucose. The ketogenic diet, which can initiate and maintain ketosis, was developed initially to treat pediatric refractory epilepsy. The original diet required ingesting calories primarily from fat, with a minimally sufficient amount of proteins to allow for growth and repair, and with a very restricted amount of carbohydrates. A typical diet would include a 4:1 ratio of fat to combined protein and carbohydrate (by weight). The ketogenic diet can allow one's body to consume fats for fuel rather than carbohydrates. Normally, the carbohydrates contained in food are stored as glycogen in the body and then, when needed, converted into glucose. Glucose is particularly important in fueling brain-function.

When a body lacks carbohydrates, the liver converts fat into fatty acids and further into ketone bodies. The ketone bodies are able to pass into the brain and replace glucose by up to 70% as the primary fuel substrate. An elevated level of ketone bodies in the blood, i.e. ketosis, has been shown to reduce the frequency of epileptic seizures. Ketosis has been shown to improve brain-function by providing a critical source of fuel to fuel starved cells due to a pathologically compromised inability to completely oxidize glucose. That pathologic inability is very likely at the root of many well-known neurodegenerative diseases such as Alzheimer's Disease, Parkinson's Disease and amyotrophic lateral sclerosis (ALS). The pathologic inability to process glucose is also very likely at the core of concussions and Traumatic Brain Injury (TBI).

In addition to improved brain-function, ketones can improve muscle performance, such as in endurance athletes, and muscle recovery that would be beneficial to all athletes, including sprinters. Skeletal muscles show a higher affinity for ketones and in particular the enantiomerically pure ketone body (D)-β-hydroxybutyrate ("(D)-β-HB") over glucose. (D)-β-HB is thermodynamically more powerful than glucose. (D)-β-HB produces more ATP per unit volume oxygen than glucose. This is because the body can only store and convert about 100-minutes worth of glycogen into useful glucose during extreme and prolonged exercise, such as in bicycle races and long-distance running. Athletes can train to extend their body's capacity, but there are limits. Moreover, a clear decline in glucose can be measured within about 16 minutes of physical exertion. Yet, with a second or alternative source of energy, from ketones, the body can continue to perform beyond the individual's capacity to utilize glucose. Further, studies have shown that ketones can improve performance by as much as eight to twelve percent.

A Ketone Blend is defined as a blend of two or more compounds described in the patent that are either comprised of a free acid of β-hydroxybutyrate, salt of β-hydroxybutyrate, ketone ester of hydroxybutyrate, or 1,3-butanediol which when taken orally shall increase serum levels of (D)-β-hydroxybutyrate.

The phrase Ketone Ester shall for the purpose of this document, be defined as one of two ketone esters. Those esters are 3-hydroxybutyl-3-hydroxybutyrate and 3-hydroxybutyl-3-hydroxy-ethyl butyrate.

The Ketone Blend containing any two or more of the above listed compounds can be in any relative concentration ratios. The preferred embodiments shall be as follows: 51-99% free acid, 1-25%—Ketone Salt, 1-10%—1,3-butanediol, and 1-49%—Ketone Ester.

Each of the compounds have chiral centers thus having (D) and (L) isomers. In a preferred embodiment all of the compounds shall be enantiomerically enriched with respect to the (D) isomer. Enantiomerically enriched shall be defined as having greater than 50% concentration, of the D isomers.

The preferred enantiomeric embodiment of the 3-hydroxybutyl-3-hydroxybutyrate diastereomer shall be comprised such that the β-hydroxybutyrate section of the 3-hydroxybutyl-3-hydroxybutyrate molecule shall be substantially enantiomerically enriched >95%-100% for the (D) isomer and the chiral alcohol used in the same 3-hydroxybutyl-3-hydroxybutyrate molecule shall be enantiomerically enriched >80%-100% for the (D) isomer The definition Ketone Salt contained in the Ketone Blend includes the salt of hydroxybutyrate with sodium, potassium, calcium and magnesium regardless of whether the reacted salt was added to the Ketone Blend or the free base of any of the aforementioned metals is combined with the free acid of hydroxybutyrate in the Ketone Blend. They are for all metabolic purposes the same product.

Metabolically and for the purpose of this document, there is no distinction between sodium-hydroxybutyrate and sodium hydroxide or sodium bicarbonate combined with or added to the free acid of hydroxybutyrate. The moment those compounds come into contact with water contained in the human body, the salt shall be inexorably formed.

This patent focuses on "partially buffered free acid." A partially buffered free acid is defined as the free acid of β-hydroxybutyrate which has been reacted with a base to form a salt using less than a 1:1 molar equivalent of the base relative to the acid. The purpose is to be able to increase the load of (D)-β-hydroxybutyrate without increasing the load of sodium, potassium, calcium or magnesium such that a person may take more jβ-hydroxybutyrate in any form without exceeding recommended safe levels for any salts in any given period.

At the same time, all people and in particular athletes, need some amount of salt for normal homeostasis and performance.

The preferred embodiment shall contain between 1-100% of the Recommended Daily Allowance (RDA) as defined by the Food and Drug Administration of the aforementioned salts while at the same time delivering 10-150 grams of (D)-β-hydroxybutyrate for an average sized man.

Achieving therapeutic levels of ketones in the blood can be difficult and/or problematic if using only racemic β-HB free acid and/or the salts of racemic β-HB. The use of pure, free acid form of β-HB at the upper limit of therapeutic doses has been considered undesirable due to the possibility of acute acidosis or gastrointestinal (GI) distress. For example, US Pre-grant Patent Publication 2006/0280721 A1, which is incorporated in its entirety herein by reference, states that "direct administration of either (R)-3-hydroxybutyrate or acetoacetate in their acid form can result in significant acidosis following rapid absorption from the gastrointestinal tract." The reference also cautions that "[a]dministration of the sodium salt of these compounds is also unsuitable due to a potentially dangerous sodium overload that would accompany administration of therapeutically relevant amounts of these compounds." (Desrochers et al. J. Nutr. Biochem. 1995, 6, 111-118) At the same time, the β-hydroxy group is unstable in the presence of low pH. Furthermore, reliance on only 1,3-butanediol, whether racemic or non-racemic, can lead to intoxication.

A solution can be a mixture of such constituents whose individual drawbacks do not compound when mixed with other individual constituents. It can be shown that specific mixtures of two or more components can safely lead to therapeutic levels of ketones in the blood. For example, in a preferred embodiment, acid and salts of enantiomerically pure or enantiomerically enriched β-HB can be advantageously combined with (D)-1,3-butanediol. To be clear, the chemical prefix "D" as used herein includes both enantiomerically enriched and enantiomerically pure versions, unless stated otherwise or used in a context that makes clear that only the pure version is intended. In alternate embodiments, both enantiomers of (D/L) 1,3 butanediol and mixtures thereof may be utilized as components of the composition to reduce production costs.

In some preferred embodiments, enantiomerically enriched salts of (D)-β-hydroxybutyrate can be specifically combined for additional efficacy with reduced, or even without, undesirable negative side effects of each part by itself. Further, a combination of these enantiomerically enriched compounds can allow for much higher levels of ketones, limiting the risk of acute acidosis, salt overload, and gastrointestinal distress, at the highest doses. In alternate embodiments, the Ketone Blend may be administered along with a Ranitidine, Famotidine, or similar stomach acid inhibitors (namely histamine H2 receptor antagonists) to increase the pH of the gut and preserve the efficacy of the compounds. Furthermore, enteric coatings and encapsulations, as known in the arts, may be used to bypass the highly acidic nature of the gut and promote the enhanced bioavailability of the compounds.

There can be several ways to increase ketone levels. As shown above, however, there can be significant drawbacks and limitations to each. Additional methods and considerations are discussed below. Nevertheless, novel and specific combinations have been discovered that can balance limitations against each other with a resulting mix that is therapeutic.

Ketosis can be induced through eating a ketogenic diet, e.g., a diet of approximately 80% fat, 15% protein, and 5% carbohydrates. Such diets are difficult to maintain and are often found to be unpalatable. Ketogenic diets are not practical for the general population. Moreover, only the strictest diets can achieve up to about 3 mmol/L of ketones. Total caloric restriction or "starvation ketosis" for 10 days or more can achieve levels as high as 8 mmol which may be considered as the upper level of endogenous nutritional ketosis, but total caloric restriction is obviously not maintainable.

Several salts of β-hydroxybutyrate can be utilized to promote ketosis. For example, the sodium, potassium, and calcium salts are each useful and, within limitations, safely ingestible. The racemic sodium salt of β-hydroxybutyrate can be consumed to promote ketosis. However, regular consumption is limited by sodium's recommended dietary allowance (RDA) and daily upper limit, for example as set forth by the Food and Drug Administration. Most Americans currently consume roughly 50% in excess of the RDA for sodium. If a person's dietary sodium is limited to only sodium β-hydroxybutyrate, then that person would be limited to approximately 0.5 mmol/L of ketones by consuming racemic sodium β-hydroxybutyrate at about 100-200% of the RDA for sodium. (See U.S. Pat. No. 9,138,420, FIG. 1) That number falls considerably short of the 8 mmol upper level of nutritional ketosis.

Figure 6:
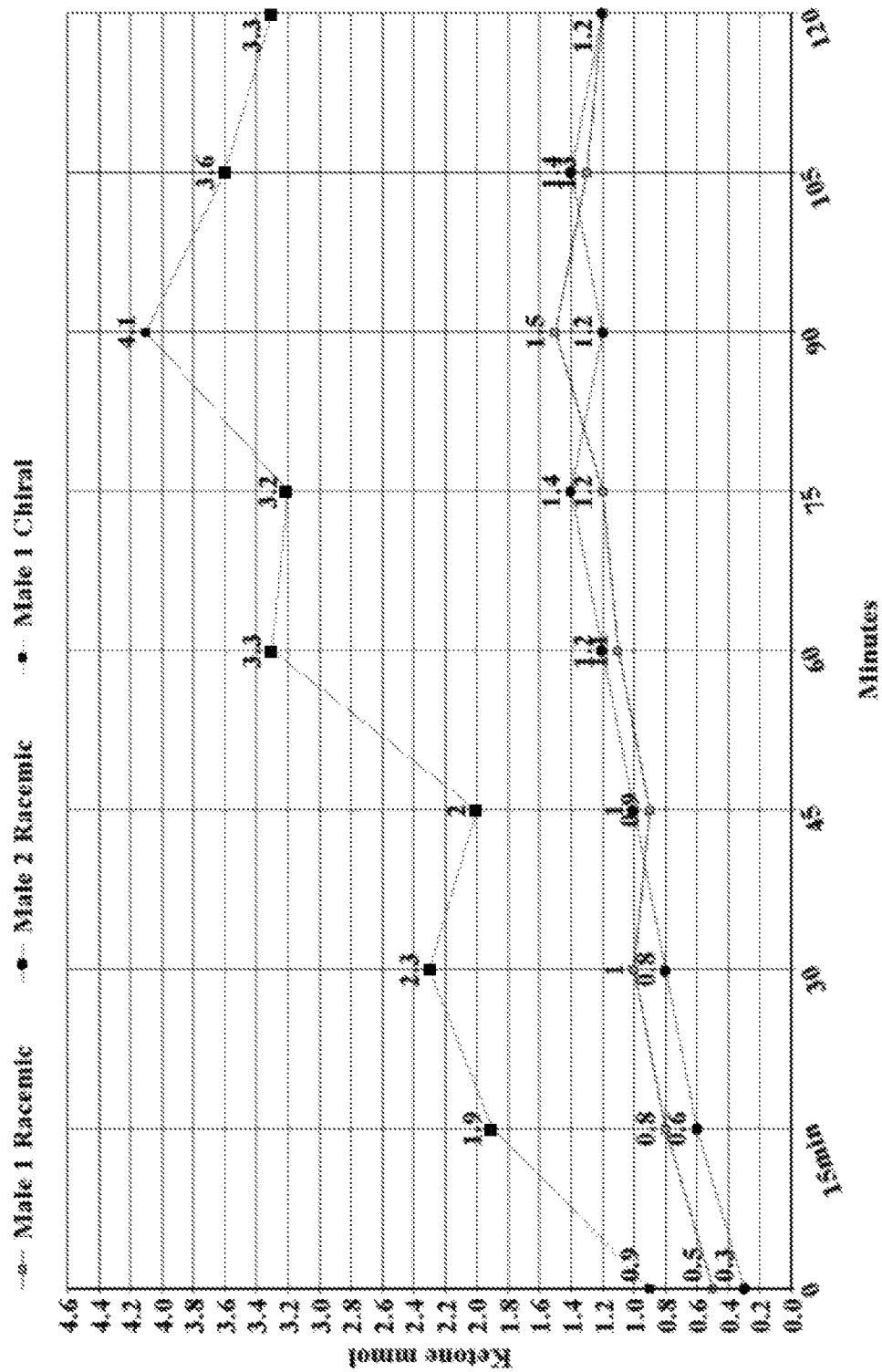
FIG. 6 depicts a ketone blood concentration after one person ingested (D)-1,3-butanediol, compared to the results of two people ingesting racemic 1,3-butanediol.
Figure 7:
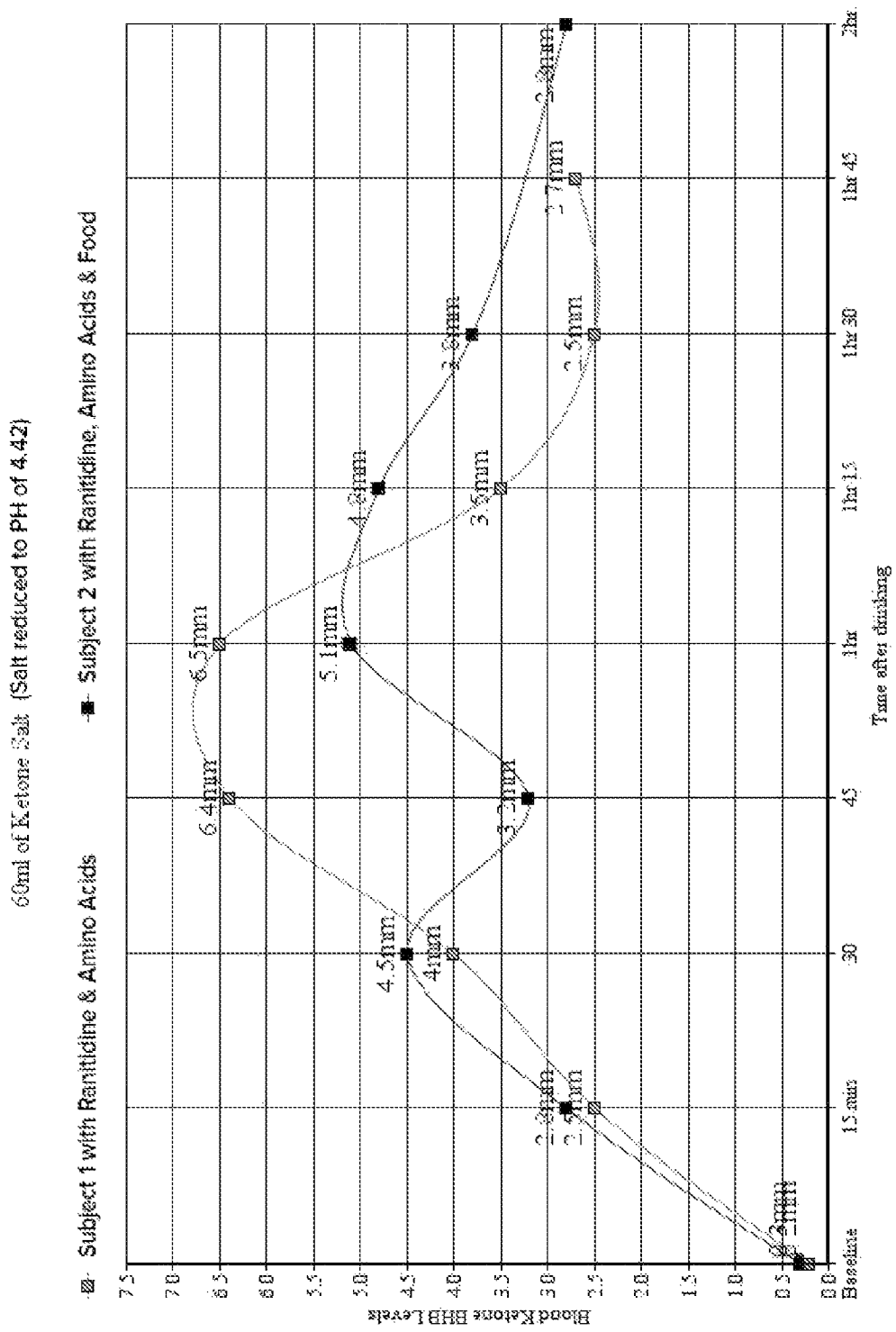
FIG. 7 depicts ketone blood concentrations in a first subject given Ranitidine and amino acids, compared with a second subject given Ranitidine, amino acids, and food.
Figure 8:
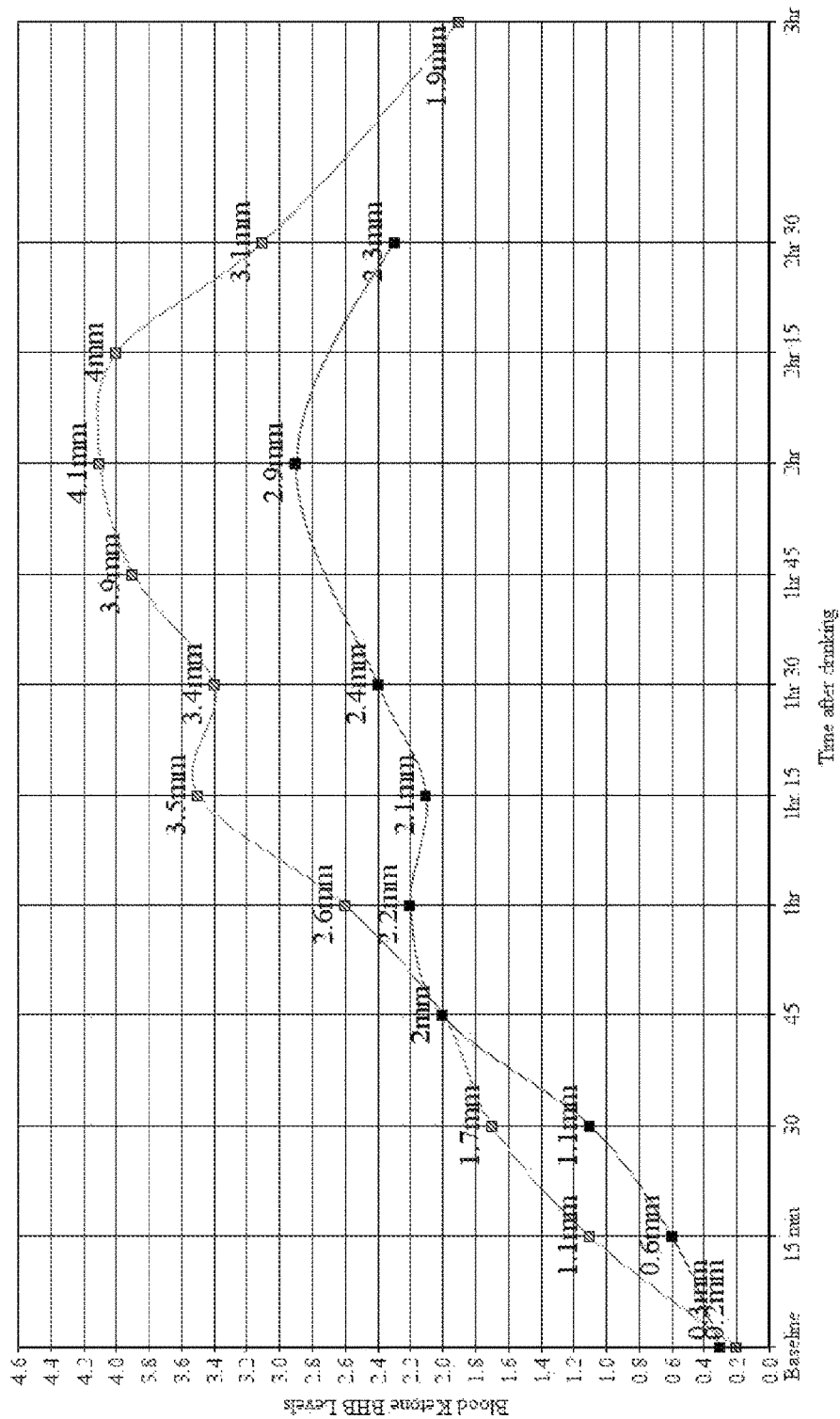
FIG. 8 depicts ketone blood concentrations in a first subject given Ranitidine 60 minutes before injection while fasting, compared with a second subject given only the fasted treatment.

It should also be noted that only the D enantiomer is active in the body as a source of extracellular fuel that is then transported into the cells. Ketone blood level meters currently on the market only measure the blood level of the D enantiomer. Products containing racemic salts require two to three times the amount of sodium, calcium and potassium for an equal amount of (D)-β-hydroxybutyrate. A reason the potential levels of (D)-β-hydroxybutyrate in the blood is over double compared with an equal amount of the racemic solutions is because the body has to waste energy and uses up some of the (D)-β-hydroxybutyrate to burn off the unnatural (L)-β-hydroxybutyrate. FIG. 6 shows the results from consuming 33 ml of enantiomerically pure (D)-1,3-butanediol are over double the amount of ketones (mmol) in the blood than that of consuming 33 ml of racemic 1,3-butanediol over a 120 minute period.

In the paragraph below, ketone mmol levels are based on racemic salts.

Potassium β-hydroxybutyrate is another salt that can be consumed to promote ketosis, but as with sodium, potassium has a RDA and upper limit (UL) that limits consumption. By consuming racemic potassium β-hydroxybutyrate at about 100% of potassium's RDA, a person would be limited to reaching approximately 0.5 mmol/L. (See U.S. Pat. No. 9,138,420, FIG. 1) Further, the potassium salt can have an undesirable metallic taste that can limit people's willingness to consume this salt alone. Moreover, there are some medications that require strict limitations on potassium intake.

Consumption of calcium β-hydroxybutyrate salt is more limited than for the sodium and potassium salts. For example, calcium's RDA is approximately 1000 mg whereas sodium's RDA is over 2000 mg and potassium's RDA is nearly 5000 mg. Nevertheless, consumption of this salt, within limitations, can promote ketosis.

The free acid of racemic β-hydroxybutyrate can also be ingested to produce ketones. While a fast acting ingredient, β-HB free acid has several problems when consumed alone.

First it is an acid, similar in acidity to that of lemon juice. Consuming too much of the free acid can degrade tooth enamel and/or cause GI problems. Also the pure free acid, a powder, can be dangerous to handle. For example, if the powder is too fine, consumers can accidentally get thus some in their eyes and/or nostrils, which can cause a burning sensation. Consumption of the free acid is also limited by tolerability of the GI tract. Encapsulation of the free acid or salt has been shown to increase pass through from the GI into the blood, thus increasing blood levels of (D)-β-hydroxybutyrate. Encapsulations and forms of enteric coating known in the arts may be utilized to help bypass the highly acidic gut and thus prevent gastric degradation of the compound. In alternate embodiments, the (D)-β-hydroxybutyrate and/or a Ketone Blend may be administered along with a Ranitidine, Famotidine, or similar stomach acid inhibitors (namely histamine H2 receptor antagonists) to increase the pH of the gut and preserve the efficacy of the compounds. At upper levels of therapeutic doses, a danger can exist for acute acidosis and overwhelming natural buffering ability of blood. For any given weight, the racemic free acid, at twice the mass of non-racemic, containing the same amount of (D)-β-hydroxybutyrate as enantiomerically pure or considerably enantiomerically enriched (D)-β-hydroxybutyrate will be twice as acidic as the pure (D)-β-hydroxybutyrate, thus limiting the amount that may be safely administered. Perhaps the most common example is ketoacidosis, in which a diabetic and/or alcoholic produces so much (D)-β-HB as to overwhelm the body's ability to buffer the acid.

Another constituent of foodstuff that can promote ketosis is 1,3-butanediol, in particular, (D)-1,3-butanediol. Constituents have been investigated by both NASA and the Department of Defence as a compact source of calories for astronauts and soldiers. (D)-1,3-butanediol by itself, however, was found to be both unpalatable and costly. However, we devised ways to reduce production costs and improve palatability. Nevertheless, consumption of (D)-1,3-butanediol can cause inebriation, which limits its ability to be a primary source for achieving ketosis. (D)-1,3-butanediol is rapidly converted in the liver to (D)-β-hydroxybutyrate. It must be emphasized that for the same effective concentration of (D)-β-hydroxybutyrate in the blood, over twice as much racemic 1,3 butanediol would have to be consumed. Thus use of the pure enantiomer of (D)-1,3-butanediol or enantiomerically enriched 1,3-butanediol would have far less side effects relative to blood levels of (D)-β-hydroxybutyrate.

Lastly, Ketone Ester can be an excellent, and previously unrivalled, driver of ketosis. But, the Ketone Ester is exorbitantly expensive. For example, a single dose of the (D/D) Ketone Ester can cost upwards of $30,000 to produce.

Preferred embodiments utilize an optimized mix of one or more of the above ingredients to maximize ketone production, yet tailor the ingredients to account for recommended limitations, palatability, and deleterious side effects. Rapid inducement and maintenance of ketosis can be achieved by utilizing certain optimized formulae that approaches the maximal efficacy of (D)-3-hydroxybutyl-(D)-3-hydroxybutyrate, but at a tiny fraction of the cost.

A preferred embodiment can include a mixture by molar ratio of 10-15 parts free acid (D)-β-HB, 10-20 parts (D)-β-HB salt, and 1 to 5 parts (D)-1,3-butanediol. The salt can be pure or, in a preferred embodiment, can be in a ratio by weight of 44% potassium salt, 32% sodium salt, and 24% calcium salt. This ratio, while not rigid, optimizes the salts according to their RDAs. Another preferred embodiment can include a mixture of, 10-15 parts free acid (D)-β-HB, 3-7 parts (D)-β-HB salt, and 1-5 parts (D)-1,3-butanediol. Again, the salts can be optimized according to consumer needs and/or FDA recommendations. The latter ratio can allow three times the dose of the former mixture while maintaining FDA recommendations for the salts. A particular preferred embodiment can include a mixture of approximately, 10 parts free acid (D)-β-HB, 8 parts (D)-β-HB salt, and 1-3 parts (D)-1,3-butanediol.

The free acid of (D)-β-hydroxybutyrate is a white, odourless crystal with a slightly tart or acidic taste. It is a mild acid with a pH between, vinegar and lemon juice. It can be formulated into most foodstuffs, e.g. drinks, puddings, mashed vegetables, and/or inert fillers. The acid forms of (D)-β-hydroxybutyrate are suitable for use orally as they have a pKa of 4.4. This is less acidic than citric acid with pKa of 3.1 and pKa2 of 4.8 and slightly more acidic than acetic acid with a pKa of 4.7.

While the use of pure, free acid form of (D)-β-hydroxybutyrate has been considered dangerous, the quantity that would have to be consumed to cause metabolic problems or GI distress would be quite high. In moderate quantities, the free acid (D)-β-hydroxybutyrate can be advantageously combined with, e.g., non-racemic salts of (D)-β-hydroxybutyrate and/or the non-racemic precursor to (D)-β-hydroxybutyrate, called (D)-1,3-butanediol, to achieve a more rapid onset of ketone bodies in the blood and higher concentrations than previously explored compositions.

Free acid (D)-β-hydroxybutyrate is a mild acid slightly weaker in strength than citric acid. One liter of grapefruit juice contains about 25 grams of citric acid. In some sensitive people that can be enough to cause gastrointestinal distress or aggravate acid reflux. Nevertheless, most people can tolerate the acidity of grapefruit juice.

Free acid (D)-β-hydroxybutyrate, like grapefruit juice, can cause problems if consumed in quantities greater than, e.g., 150 grams per day or in acute doses above 20-40 grams dissolved in a small amount of water. The average human will produce a maximum of 150 grams in 24 hours during starvation level ketosis. That same amount can be considered a maximum therapeutic amount of any form of (D)-β-hydroxybutyrate. It can be dangerous to deliver 150 net grains of (D)-β-hydroxybutyrate in the racemic form, and no safety data has been published regarding any racemic compounds of β-hydroxybutyrate. In a preferred embodiment of 40% (molar percentage) (D)-β-HB in its free acid form, 40% (D)-β-HB salt, and 10% (D)-1,3 butanediol, a 30 gram serving contains approximately 6 grams of the free acid of (D)-β-HB, or not more than the acid load in a single 250 ml drink of grapefruit juice.

Another benefit of preferred combinations that include free acid (D)-β-hydroxybutyrate is that the free acid can be used directly by the body without having to be processed in the liver and can easily cross the blood-brain barrier. Preferred embodiments can raise ketones in the blood more rapidly than precursors or derivatives. Free acid (D)-β-hydroxybutyrate, in levels tolerated by the GI system, can be part of preferred compositions. A major advantage is that embodiments, unlike previous compositions (sometimes administered intravenously or topically), can be orally administered, which is less expensive and easier for the patient.

Preferred compositions can be designed to reach target levels of 2.5-10.0 mmol/L of ketones in the blood. It has been shown that elite athletes can achieve an average of two percent and up to an twelve percent improvement in performance with 5.6 mmol/L or higher (See, for example, www.cell.comicell-metabolism/fulltext/S1550-4131(16) 30355-2). In a long term case study with an Alzheimer's patient, an obvious correlation in the mitigation of symptoms was made once blood levels reached 3-7 mmol/L.

(D)-β-hydroxybutyrate is thermodynamically more energy dense than glucose. The oxidation of (D)-β-hydroxybutyrate per unit volume of oxygen produces more energy than glucose, A direct correlation between the concentration in the blood to a minimum threshold and physical performance can be shown. Based on studies involving rats' hearts, Alzheimer's patients, and other studies, it may be shown that ketone concentrations in the blood above various threshold minima can provide therapeutic effects for a variety of neurological conditions such as Alzheimer's, Parkinson's, ALS, Multiple Sclerosis, traumatic brain injury, epilepsy, and autism, as well as non-neurological conditions such as diabetes types I & II. For example, (D)-β-hydroxybutyrate has been shown to act as a fuel substrate and substitute for glucose in diabetics as well as have hormone-like effects such as lowering of insulin levels.

While certain components within preferred embodiments have been investigated for their therapeutic value, it is important to note that each component within preferred embodiments is a. foodstuff, not a pharmaceutical drug. Moreover, metabolic therapies have been investigated to provide mitochondria a source of energy needed to promote normal healthy metabolism in all people, healthy and otherwise. For example, U.S. Pat. No. 6,207,856, which is incorporated herein in its entirety, discusses administration of metabolic precursors in amounts sufficient to raise ketone bodies in blood. See Col. 5. The '856 patent explains that elevated levels of ketone body concentrations in the blood can result in not only maintenance of cell viability but improved cell function and growth beyond that of normal. The reference, however, fails to recognize or suggest present embodiments and, resultantly, fails to achieve the benefits of present embodiments. Several benefits of increased ketone bodies in healthy individuals can include nerve stimulant factors, i.e. nerve growth factors and factors capable of stimulating enhanced neuronal function, such as increased metabolic rate, retardation of degradation, and increased functional features such as axons and dendrites.

The rapidity of onset of available ketones in the blood can be of particular concern, for example to diabetics and/or athletes. Preferred embodiment can safely induce ketosis more rapidly than previously thought possible. For example, U.S. Pat. No. 9,138,420 shows that a peak concentration of blood concentrations of (D)-β-hydroxybutyrate produced by consuming a combination of (D/L)-β-hydroxybutyrate salt and MCT (medium chain triglycerides) oil required up to 3 hours. Further, both subjects fasted prior to testing, which naturally increases ketone levels. For example, the subject who reached 1.3 mmol/L began the trial at 0.2 mmol/L. Thus, the net rise in ketones was approximately 1.1 mmol/L. The second subject began the trial at 0.9 thus the net rise in ketones was only about 1.65 mmol/L. What is more, each of the above trials required sodium consumption of approximately 2 grams. Reaching a target of 5-7 mmol/L in a 70 kg adult using previous compositions would require approximately 16 g of sodium, far exceeding the daily recommended amount of 2.3 g per day. In addition, MCT oil is not tolerated well by the gut and can require an adaptation phase.

As presented herein, the use of "consuming" may include oral and/or parenteral delivery of the ketones in order to raise blood ketone levels in a user. Dosing protocols may be simply defined as up to 2 g/kg of body weight per day for the user. Dosing of the 2 g/kg may be partitioned throughout the day, or taken all at once.

Present embodiments can provide and/or lead to many benefits. For example, the Ketone Blend can be utilized to induce erections in men with erectile dysfunction. Nitric oxide (NO) is believed to be a main vasoactive mediator of penile erection. (See, e.g., website: onlinelibrary.vviley.com/doi/10.1111/j.1524-6175.2006.06026.x/full Dec. 8, 2006) (D)-β-hydroxybutyrate can increase serum NO. (D)-β-hydroxybutyrate has been shown to increase serum levels of Nitric Oxide (NO), NO is the active metabolite shown to cause vasodilation in capillaries and aid in gaining an erection. The dose should be 7 minutes to 60 minutes prior to initiation of sex. The dosing protocol should be a single dose of 100-750 mg/kg body weight or between 7-52 grams for a 70 kg male. Can be taken up to twice per day but not to be taken more than once in any 4 hours.

Present embodiments can also be useful in treating hair loss, vision impairment, amyotrophic lateral sclerosis (commonly referred to as ALS or Lou Gehrig's disease), concussions, heart disease, diabetes, and traumatic brain injury, in addition to enhancing physical performance.

A method of treating hair loss may include the steps of, after ten weeks of daily doses of 20 grams, three times per day, an elderly person began growing back the pubic hair. it is believed that 5-50 grams per dose, throughout the day for a total of between 15-150 grams per day for at least ten weeks will have a similar effect on the hair follicles on the heads of persons suffering hair loss or male pattern baldness.

A method of treating increasing visual acuity is disclosed. Ketone Ester and/or Ketone Blend has shown to produce immediate increases in visual acuity and depth perception for up to 4 hours. Individuals should consume between 5-50 grams to improve vision. Can be taken continually throughout the day. Not to exceed 150 grains in any 24 hours.

Persons suffering with ALS display chronic fatigue and chronic cognitive impairment. The mechanism of impairment has been traced to an impairment with pyruvate dehydrogenase in the mitochondria. Cells of the central nervous system, the heart and skeletal muscles, due to the impairment, lack the critical energy or ATP to function normally. (D)-β-hydroxybutyrate circumvents the pyruvate dehydrogenase impairment and provides for far higher energy and ATP creation in those cells. Upon ingestion, relief from symptoms such as fatigue and cognitive impairment are significantly reduced within 15 minutes of ingestion and last from between 2 and 6 hours, during which time, those persons have noticeably increased energy, cognitive function and myocardial efficiency. The dosing regimen should be between 5-60 grams 1-3 times per day with the preferred amount to be between 20-40 grams 3 times per day.

The mammalian pyruvate dehydrogenase complex (PDHC) is a mitochondrial matrix enzyme complex (greater than 7 million Daltons) that catalyzes the oxidative decarboxylation of pyruvate to form acetyl CoA, nicotinamide adenine dinucleotide (the reduced form, NADH), and $CO_2$. This reaction constitutes the bridge between anaerobic and aerobic cerebral energy metabolism. PDHC enzyme activity and immunoreactivity are lost in selectively vulnerable neurons after cerebral ischemia and reperfusion. Evidence from experiments carried out in vitro suggests that reperfusion-dependent loss of activity is caused by oxidative protein modifications. Impaired enzyme activity may explain the reduced cerebral glucose and oxygen consumption that occurs after cerebral ischemia. This hypothesis is supported by the hyperoxidation of mitochondrial electron transport chain components and NADH that occurs during reperfusion, indicating that NADH production, rather than utilization, is rate limiting. Additional support comes from the findings that immediate postischemic administration of acetyl-1-carnitine both reduces brain lactate/pyruvate ratios and improves neurologic outcome after cardiac arrest in animals. As acetyl-1-carnitine is converted to acetyl CoA, the product of the PDHC reaction, it follows that impaired production of NADH is due to reduced activity of either PDHC or one or more steps in glycolysis. Impaired cerebral energy metabolism and PDHC activity are associated also with neurodegenerative disorders including Alzheimer's disease and Wernicke-Korsakoff syndrome, suggesting that this enzyme is an important link in the pathophysiology of both acute brain injury and chronic neurodegeneration. (D)-β-hydroxybutyrate has been shown to circumvent the impairment of PDHC, to provide the critical source of energy needed by traumatized neurons in order to function. Additionally, (D)-β-hydroxybutyrate is a very powerful antioxidant for reactive nitrogen and oxygen species believed to cause cell death through oxidative stress. Persons should begin taking (D)-β-hydroxybutyrate and/or Ketone Blend at the first indication of brain trauma or suspected trauma. Depending on the severity of the trauma, patients may be required to take the (D)-β-hydroxybutyrate and/or Ketone Blend for 1 week-8 weeks. In particularly severe cases or when individuals suffer multiple traumas such in professional football, the damage to cells may be permanent and progressive which is suspected in some football players. In those cases, (D)-β-hydroxybutyrate and/or Ketone Blend should be taken for the rest of their lives. Dosing protocols should try and provide the most constant level of (D)-β-hydroxybutyrate in the blood, as possible. This may be encouraged with a particular combination of Ketone Ester and encapsulated free acid using an enteric coating designed to dissolve at different rates through the length of the entire GI system over 8 hours. This particular embodiment would be preferred to be taken at 375 mg/kg, 2 times per day which for an average 70 kg man would be approximately 26 grams, 2 times per day. Ranges could be between 5-50 grams, 2-3 times per day for the average man, but significantly more for a football player that weighs much more. Using non-encapsulated or non-coated free acid, it would be preferred to take more smaller doses up to 8 times per day with doses of 2-20 grams per dose.

(D)-β-hydroxybutyrate has been shown to increase ATP production over glucose for the same volume of air. For every breath, athletes substituting (D)-β-hydroxybutyrate over glucose produce more energy per breath increasing average energy output. However, due to the fact that (D)-β-hydroxybutyrate significantly lowers blood sugar, total energy output above the anaerobic threshold may suffer. As a consequence, athletes taking (D)-β-hydroxybutyrate for greater performance and endurance must compensate for lowered blood sugar by taking supplemental glucose. Due to the complex interaction between glucose, insulin and ketones, the glucose must be taken 10-60 minutes prior to the ketones, preferably between 15-25 minutes prior. Glucose supplementation should be between 0.5 to 2 times the amount of ketones. The range of ketones should be between 200-1,000 mg/kg body weight, which for an average 70 kg person would be 14-70 grams just prior to the onset of physical activity or between 0-60 minutes prior to the onset of physical activity. The amount of glucose taken prior to the ketones would be between 14 and 140 grams. The greatest increase in physical activity will be just after ingestion of ketones and last between 1-4 hours. Athletes may take the ketones up to twice per day with total ketone addition not to exceed 150 grams per day.

Acute concussion and the associated impairment of PDHC results in glucose being only partially metabolized and heat as a byproduct of incomplete oxidative respiration. Acutely traumatized areas of the brain see an increase in temperature of approximately 1 degree. Modern handheld Forward Looking Infrared Red (FLIR) technology is sensitive enough to detect increases of 0.1 degree and provide a visual diagnostic method to diagnose acute brain trauma.

Therapies can be improved by limiting dietary carbohydrates and/or protein. Therapies to treat the above and/or other maladies can be part of an iterative process. Specifically, after administering or consuming an embodiment, blood levels of ketone bodies and/or anions of the salts can be measured. In a preferred method any combination of the Ketone Blend can be administered. Then, the patient's blood levels can be measured for ketone bodies and/or salt levels. Based on the measurements, the dosage can be tuned to the particular patient. For example, if a patient's ketone levels are only reaching 0.3 mmol/L, then the dosage can be increased. As another example, the patient's ketone levels may be at 5.0 mmol/L but the patient's salt levels may be alarmingly high. In the latter example, the combination of constituents can be altered to reduce the salt or the entire dose can be reduced.

Present embodiments can also be utilized to address muscle recovery, cancer, autism, fibromyalgia, chronic pain, migraines, stroke, multiple sclerosis, aging, epilepsy, diabetes, weight loss, radiation poisoning, Autism, ADD, Alzheimer's, and Parkinson's. For example, Alzheimer's and Parkinson's diseases, the brain is unable to completely metabolize glucose, which leads to a host of problems. Ketones, however, can provide an alternative fuel source in the brain to carry out normal metabolic processes. In particular, the mitochondria in the brain can be fueled with ketones and halt and/or reverse the effects of those diseases (and other diseases where the brain is unable to metabolize glucose).

Apart from disease, present embodiments can provide additional clarity of mind and improved energy levels by safely increasing ketone bodies in the blood, Embodiments can treat radiation poisoning and protect against radiation by quenching the reactive oxygen species and reactive nitrogen species and shutting down superoxide production by eNOS and DUOX which are partly responsible for the cycle that causes radiation damage to persist.

Nutritional ketosis has not previously been sustainable in different contexts. For example, metabolization of ketones can vary based on the metabolic rate of a particular individual. As another example, an athlete can burn a concentration of 6 mmol/L to less than 1 mmol/L in as little at 75 minutes of exertion. Prior thoughts have been to buffer the free acid with sodium salts. See, e.g., U.S. Pat. No. 9,138,420. But, this can cause harmful sodium overload and mineral imbalance, especially to achieve therapeutic levels of ketosis. Prior attempt have also failed to appreciate the importance of specific combinations that present embodiments include. For example, the '420 patent is directed to β-hydroxybutyrate in general as a compound and lists scores of β-hydroxybutyrate compounds as potential precursors, but fails to appreciate which compounds are efficacious or even safe (e.g. listing a lithium salt that can be dangerous). And further, it fails to appreciate the superiority of utilizing non-racemic compounds and mistakenly suggests that racemic compounds are as efficacious as enantiomerically enriched or pure compounds. Worse yet, it explicitly states that "oral administration of βHB and acetoacetate in their free acid form is expensive and ineffective at producing sustained ketosis," which is contrary to our findings with present embodiments. To address prior problems, preferred embodiments can increase ketone concentration in the blood more rapidly than previously thought possible to do safely. Indeed, present embodiments are a stark departure from previous paradigms and attempts to induce and maintain ketosis. For example, by using an enantiomerically enriched, non-racemic salt (D)-β-hydroxybutyrate such as sodium, potassium or calcium, the amount of salt and mineral imbalance can be cut in half compared to racemic salts, yet achieve improved results. Further reductions in what have previously been considered harmful levels of salt and minerals can be achieved by incorporating the free acid of (D)-β-hydroxybutyrate at, e.g., a ratio of 20% of the total compound. Additional, or alternative, reductions can be achieved by using (D)-1,3-butanediol and/or Ketone Ester.

In an embodiment, a combination of the three ingredients can be 40% molar ratio of the sodium and/or potassium and/or calcium salt or a mixture thereof, 10% molar ratio of (D)-1,3-butanediol, and 40% of the free acid form of (D)-β-hydroxybutyrate. The ratios of this embodiment can be altered as one of ordinary skill in the art will appreciate based on the teachings herein to achieve preferred results. For example, one achievable result can be safe therapeutic levels of ketones above 2.5 mmol/L.

Present embodiments also address another problem with prior attempts. For example, the utilization of the (D) isomer of 1,3-butanediol has been cost prohibitive. Enantiomerically pure or enantiomerically enriched (i.e. greater than 50% but less than 100% form) 1,3-butanediol can provide greater results than racemic 1,3-butanediol, e.g., up to and over twice the efficacy of racemic 1,3-butanediol, Accordingly, a preferred embodiment can include, enantiomerically enriched or pure, (D)-1,3-butanediol to achieve improved results. For example, a preferred embodiment can include free acid (D)-β-hydroxybutyrate and (D)-1,3-butanediol, which can provide twice as much of bioreactive agents as racemic compositions. Enantiomerically pure β-HB, specific precursors or derivatives can be at least twice as effective as their racemic counterparts.

Figure 5:
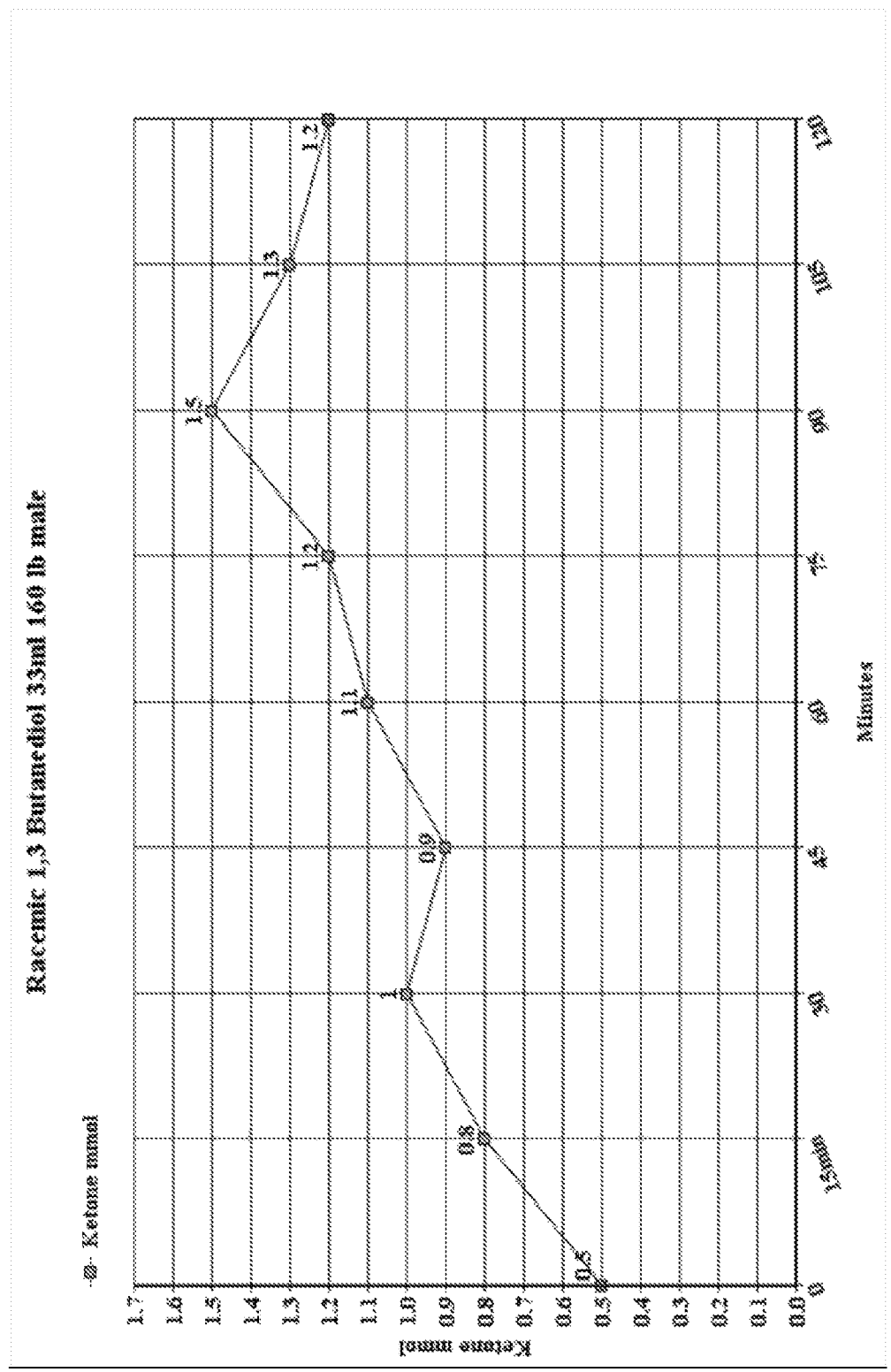
FIG. 5 depicts an exemplary ketone blood concentration after ingestion of racemic 1,3-butanediol.

FIG. 5 depicts exemplary results from ingestion of 33 ml racemic 1,3-butanediol. As can be seen, racemic 1,3-butanediol alone achieved as much as 1 mmol/L over a 105-minute period. FIG. 6, on the other hand, shows that ingestion of non-racemic (D)-1,3-butanediol can have markedly improved efficacy in achieving ketosis. For example, as shown, 33 ml of the non-racemic (D) form provided an increase in ketones of approximately 3.2 mmol/L whereas the racemic form provided approximately 0.9-1.0 mmol/L increases over pre consumption ketone As one skilled in the art will appreciate, embodiments of the present invention may be embodied as, among other things, a composition of matter and a method for making compositions of matter. Other embodiments are within the scope of the following claims. For example, while persons and patients are described herein, many advantages of embodiments can be provided to other animals, such as livestock, pets, horses, and work animals.

I claim:

1. A foodstuff comprising a mixture of β-hydroxybutyric acid salts; β-hydroxybutyric acid; 1,3-butanediol; and a ketone ester, wherein the β-hydroxybutyric acid; the salts of β-hydroxybutyric acid; 1,3-butanediol; and ketone ester are present in a molar ratio of 5:5:1:5; 5:5:2:5, or 10:5:2:5.

2. The food stuff of claim 1 wherein the ketone ester is 3-hydroxybutyl 3-hydroxybutanoate

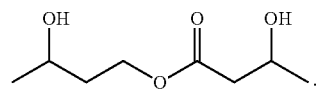

3. The foodstuff of claim 1, wherein the mixture of β-hydroxybutyric acid salts comprises at least two of sodium β-hydroxybutyrate, calcium β-hydroxybutyrate, potassium β-hydroxybutyrate, and magnesium β-hydroxybutyrate.

4. The foodstuff of claim 1, wherein β-hydroxybutyric acid and the salts of β-hydroxybutyric acid are enantiomerically enriched with respect to the D form or are in the enantiomerically pure D form.

5. The foodstuff of claim 2, wherein 3-hydroxybutyl 3-hydroxybutanoate is (D)-3-hydroxybutyl (D)-3-hydroxybutanoate,

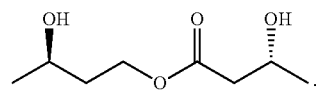

6. The food stuff of claim 1, wherein the 1,3-butanediol is racemic, enantiomerically pure (D)-1,3-butanediol, or wherein the 1,3-butanediol is enriched with respect to (D)-1,3-butanediol.

7. A foodstuff comprising:
a. about 1% to about 49% ketone ester
b. β-hydroxybutyric acid
c. about 1% to about 25% of a mixture of β-hydroxybutyric acid salts, wherein the mixture of salts comprises at least two of sodium β-hydroxybutyrate, calcium β-hydroxybutyrate, potassium β-hydroxybutyrate, and magnesium 3-hydroxybutyrate;
wherein the salts of β-hydroxybutyric acid and β-hydroxybutyric acid are enantiomerically enriched with respect to the D form or are in the enantiomerically pure D form,

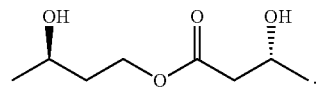

8. The foodstuff of claim 7 wherein the ketone ester is (D)-3-hydroxybutyl (D)-3-hydroxybutanoate.

9. The foodstuff of claim 7, wherein the mixture of salts comprises at least two of sodium β-hydroxybutyrate, calcium β-hydroxybutyrate, potassium β-hydroxybutyrate, and magnesium β-hydroxybutyrate.

* * * * *